United States Patent
Flier et al.

(10) Patent No.: US 6,313,098 B1
(45) Date of Patent: *Nov. 6, 2001

(54) METHODS OF NEUROENDOCRINE REGULATION OF AFFECTIVE DISORDERS

(75) Inventors: Jeffrey S. Flier, West Newton, MA (US); Julio Licinio de Castro Paixao, Beverly Hills, CA (US); Philip W. Gold, Washington, DC (US); Ma-Li Wong, Beverly Hills, CA (US)

(73) Assignees: Beth Israel Deaconess Medical Center, Inc., Boston, MA (US); The United States of America as represented by the Department of Health and Human Services, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/618,781

(22) Filed: Jul. 18, 2000

Related U.S. Application Data

(63) Continuation of application No. PCT/US99/01077, filed on Jan. 19, 1999, which is a continuation-in-part of application No. 09/009,429, filed on Jan. 20, 1998, now Pat. No. 5,866,547.

(51) Int. Cl.$^7$ ............... A61K 38/00; A61P 25/24
(52) U.S. Cl. .................................................. 514/21
(58) Field of Search ................................. 514/21

(56) References Cited

U.S. PATENT DOCUMENTS

| | | | |
|---|---|---|---|
| 4,612,132 | 9/1986 | Wollenberg et al. | 252/51.5 |
| 5,552,522 | 9/1996 | DiMarchi et al. | 530/324 |
| 5,552,523 | 9/1996 | Basinski et al. | 530/324 |
| 5,552,524 | 9/1996 | Basinski et al. | 530/324 |
| 5,643,873 | 7/1997 | Barrett et al. | 514/12 |
| 5,654,276 | 8/1997 | Barrett et al. | 514/13 |
| 5,668,181 | 9/1997 | Youdim et al. | 514/657 |
| 5,756,461 | 5/1998 | Stephens | 514/12 |
| 5,773,416 | 6/1998 | Chehab | 514/21 |
| 5,866,547 | 2/1999 | Flier et al. | 514/21 |

FOREIGN PATENT DOCUMENTS

| | | |
|---|---|---|
| WO 96/05309 | 2/1996 | (WO) |
| WO 98/36767 | 8/1998 | (WO) |

OTHER PUBLICATIONS

Kling, M.A. et al., "Effects of Electroconvulsive Therapy on the CRH–ACTH–Cortisol System in Melancholic Depression: Preliminary Findings," *Psychopharmacology Bulletin* 30(3):489–494 (1994).

Gold, P.W. et al., "Corticotropin Releasing Hormone in the Pathophysiology of Melancholic and Atypical Depression and in the Mechanism of Action of Antidepressant Drugs," *Ann. N.Y. Acad. Sci* 771:716–729 (1995).

Lam, R.W. and Stewart, J.N., "The Validity of Atypical Depression in DSM–IV," *Comprehensive Psychiatry* 37(6):375–383 (1996).

Licinio, J. et al., "Human leptin levels are pulsatile and inversely related to pituitary–adrenal function," *Nature Medicine* 3(5):575–579 (1997).

Cohen, L.J., "Rational Drug Use in the Treatment of Depression," *Pharmacotherapy* 17(1):45–61 (1997).

Wong, M.–L. et al., "Identification of Hypothalmic Transcripts Upregulated by Antidepressants," *Biochemical and Biophysical Research Communications* 229:275–279 (1996).

Torpy, D.J. et al., "The three–way interactions between the hypothalamic–pituitary–adrenal and gonadal axes and the immune system," *Baillier's Clinical Rheumatology* 10(2):181–198 (1996).

Gold, P.W. et al., "Stress system abnormalities in melancholic and atypical depression: Molecular, pathophysiological, and therapeutic implications," *Molecular Psychiatry* 1:257–264 (1996).

Licinio, J., et al., "Role of corticotrophin releasing hormore 41 in depressive illness," *Bailliere's Clinical Endocrinology and Metabolism* 5(1):51–58 (1991).

Gold, P.W. et al., "Clinical and Biochemical Manifestations of Depression: Relation to the Neurobiology of Stress (Second of Two Parts)," *The New England Journal of Medicine* 319(7):413–420 (1988).

Gold, P.W. et al., "Clinical and Biochemical Manifestations of Depression: Relation to the Neurobiology of Stress (First of Two Parts)," *The New England Journal of Medicine* 319(6):348–353 (1988).

Licinio, J. et al., "Synchronicity of frequently sampled, 24–h concentrations of circulating leptin, luteinizing hormone, and estradiol in healthy women," *Proc. Natl. Acad. Sci. USA* 95:2541–2546 (1998).

Deuschle, M. et al., "Plasma Leptin in Depressed Patients and Health Controls," *Horm. Metab. Res.* 28:714–717 (1996).

Comings, D.E. et al., "Genetic variants of the human obesity (OB) gene: Association with body mass index in young women, psychiatric symptoms, and interaction with the dopamine $D_2$ receptor (DRD2) gene," *Molecular Psychiatry* 1:325–335 (1996).

Hagerty, B.M., "Advances in Understanding Major Depressive Disorder," *Journal of Psychosocial Nursing* 33(11):27–34 (1995).

Dorn, L.D., et al., "Psychopathology in patients with endogenous Cushing's syndrome: 'Atypical' or melancholic features," *Clinical Endocrinology* 43:433–442 (1995).

(List continued on next page.)

Primary Examiner—Raymond Henley, III
(74) Attorney, Agent, or Firm—Hamilton, Brook, Smith & Reynolds, P.C.

(57) ABSTRACT

Methods of treating an affective disorder in an individual are disclosed. Affective disorders include major depression, melancholic and atypical subtypes, and dysthymia.

6 Claims, 5 Drawing Sheets

OTHER PUBLICATIONS

Nemeroff, C.B., "The corticotropin–releasing factor (CRF) hypothesis of depression: New findings and new directions," *Molecular Psychiatry* 1:336–342 (1996).

Gold, P.W., et al., "Responses to Corticotropin–Releasing Hormone in the Hypercortisolism of Depression and Cushing's Disease," *N.E. J. of Medicine*, 314(21) : 1329–1335 (1986).

Schwartz, M.W., et al., "Cerebrospinal Fluid Leptin Levels: Relationship to the Plasma Levels and to Adiposity in Humans," *Nature*, 2(5) : 589–593 (1996).

Vale, W., et al., "Characterization of a 41–Residue Ovine Hypothalamic Peptide That Stimulates Secretion of Corticotropin and β–Endorphin," *Science*, 213: 1394–1397 (1981).

"Drug Treatment of Disorders of Mood" In *The Pharmacological Basis of Therapeutics*, Eighth Edition, Goodman and Gillman's, eds. (NY: Pergamon Press), pp. 422 (1990).

"Mood Disorders." In *Diagnostic and Statistical Manual of Mental Disorders*, Fourth Edition, American Psychiatric Association, eds. (D.C.:American Psychiatric Association) pp. 317–391 (1994).

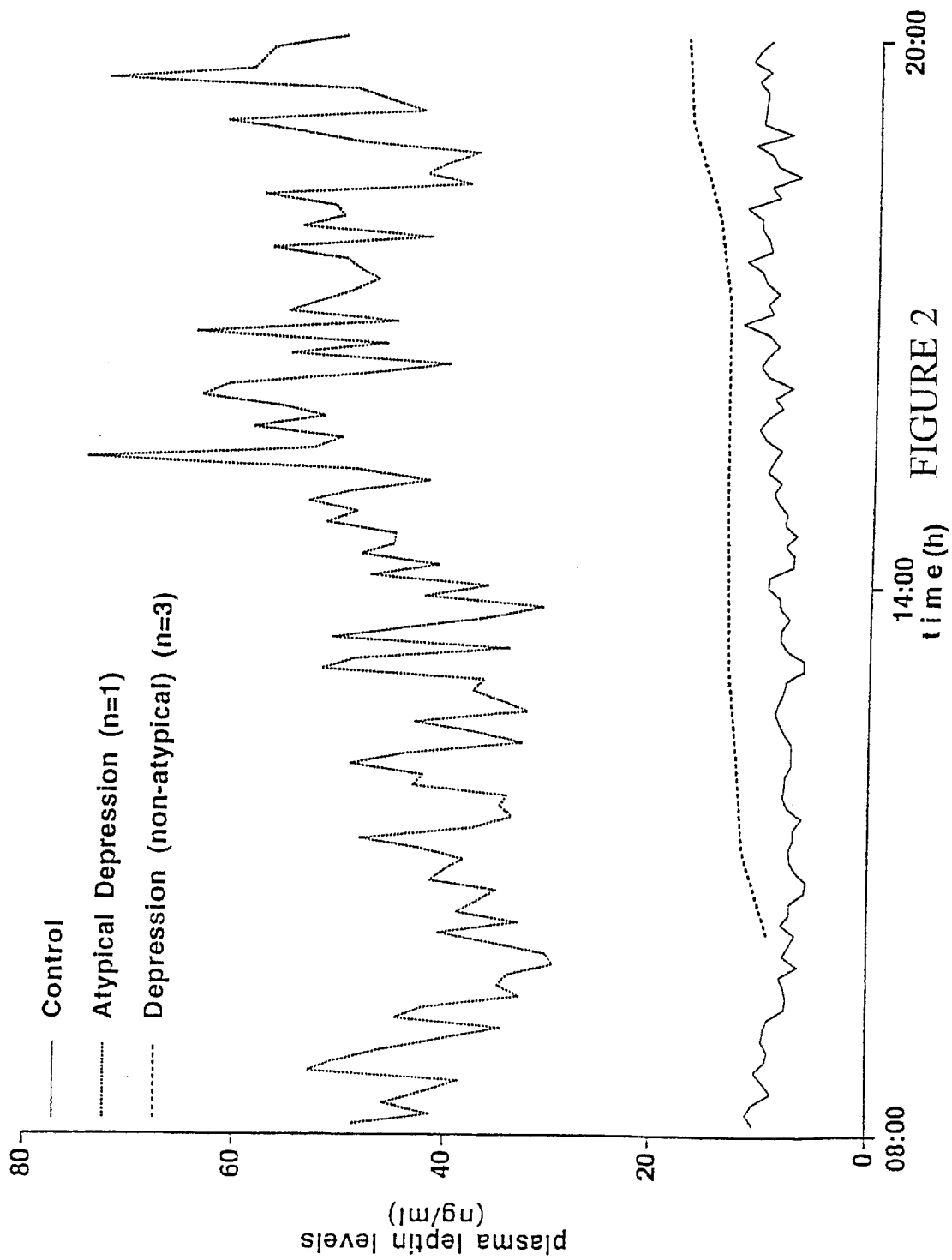

METHODS OF NEUROENDOCRINE REGULATION OF AFFECTIVE DISORDERS

RELATED APPLICATIONS

This application is a Continuation of PCT/US99/01077, filed Jan. 19, 1999, designating the U.S., which is a Continuation-In-Part of U.S. application Ser. No. 09/009,429, filed on Jan. 20, 1998, now U.S. Pat. No. 5,866,547, issued Feb. 2, 1999, the entire teachings of which are incorporated herein by reference.

GOVERNMENT SUPPORT

This invention was supported, in whole or in part, by the National Institutes of Health. The United States Government has certain rights in the invention.

BACKGROUND OF THE INVENTION

Affective and mood disorders are included in a group of mental disorders characterized by neuroendocrine dysregulation and are characterized by a disturbance in the regulation of mood, behavior, and affect. Affective and mood disorders can have serious impact on an individual's functional ability, interpersonal relationships and behavior. Major depression and dysthymia are examples such disorders.

Major depression is a syndromal, episodic and recurrent illness with both psychological and biological components. A diagnosis of bipolar disorder is given to those patients with recurring depression and mania. Those patients with recurrent depression alone have a unipolar pattern. Within the spectrum of depressive illness, there are two distinct subtypes: melancholic depression and atypical depression (Gold et al., *N. Engl. J. Med.*, 319:348–353 (1988); and Gold et al., *N. Engl. J. Med.*, 319:413–420 (1988)).

Melancholic depression is equally common among those with a pattern of unipolar and bipolar depression. Melancholic depression is characterized by hyposomnia (early morning awakening), anorexia and diurnal variation in mood, and is associated with a state of hyperarousal in which patients are painfully preoccupied with personal inadequacy, loss, feelings of worthlessness, guilt and suicidal ideation (Licinio et al., *Bailliere's Clin. Endocrin. Met.*, 5(1):51–58 (1991)).

Atypical depression is more common in bipolar patients than in unipolar depressed patients. Atypical depression is characterized by a state which seems to be opposite to that of melancholic depression. Patients with atypical depression have a syndrome of lypoarousal with hypersomnia, hyperphagia, weight gain and mood liability (Licinio et al., *Bailliere's Clin. Endocrin. Met.*, 5(1):51–58 (1991)).

Neuroendocrine dysregulation, specifically changes in the hypothalamic-pituitary-adrenal (HPA) axis, has been investigated as a biological correlate of depression. Overall, the HPA axis regulates physiologic responses to stress. The hypothalamus controls endocrine functions and the autonomic nervous system. It is involved in behaviors related to fight, flight, feeding and mating, many of which are altered during episodes of depression. The hypothalamus releases corticotrophic-releasing hormone (CRH) in response to stress, which then stimulates the anterior pituitary to secrete adrenocorticotrophic-releasing hormone (ACTH). ACTH prompts the adrenal cortex to release cortisol which, through elaborate feedback mechanisms signals the hypothalamus to increase or decrease CRH production.

Under ordinary circumstances, activation of hypothalamic CRH is terminated rapidly by the negative feedback of rising glucocorticoid levels. However, in melancholic depression, hypercortisolism does not adequately restrain the production of CRH in the hypothalamus. Thus, in melancholic depression, CRH levels are chronically elevated causing hyperactivity of the HPA axis, hypercortisolism and ACTH levels that are numerically normal, but excessive in the context of high levels of circulating cortisol (Gold et al., *N. Engl. J. Med.*, 314:1329–1335 (1986)). Antidepressant treatments consistently lower HPA axis activity in individuals with melancholic depression. In contrast, atypical depression is associated with hyposccretion of hypothalamic CRH. Thus, in atypical depression, hypothalamic CRH levels are lower than normal causing hypoactivity of the HPA axis. For a review, see Gold et al., *Mol. Psychiatry*, 1:257–264 (1996).

Dysthymia is a chronic disorder characterized by symptoms that include poor appetite or overeating, low energy (decreased arousal), insomnia or hypersomnia, and poor concentration. These functions are modulated by neuropeptides in the brain, such as CRH (Vale, W. et al., *Science*, 213:1394–1397 (1981)). Generally, dysthymia is characterized by hypothalamic CRH levels that are higher than normal, thereby causing hyperactivity of the HPA axis. However, in dysthymia, hypothalamic CRH levels can be lower than normal, causing hypoactivity of the HPA axis, in individuals with a higher than normal body mass index (BMI). Thus, in dysthymia, hypothalamic CRH levels are inversely related to the BMI of the individual.

Effective disorders are extremely common in general medical practice, as well as in psychiatry. The severity of these conditions covers an extraordinarily broad range, from normal grief reactions to severe, incapacitating, and sometimes fatal psychosis.

The lifetime risk of suicide in major affective disorders is about 10 to 15%, but this statistic does not begin to represent the morbidity and cost of this group of under-diagnosed illnesses. Typically these disorders are treated with antidepressant agents or lithium salts (GOODMAN AND GILMAN'S THE PHARMACOLOGICAL BASIS OF THERAPEUTICS, Eight Ed., 1990; Pergramon Press, New York, N.Y.). Nevertheless, many shortcomings and problems continue to be associated with all drugs used to treat affective disorders. In addition to less than-dramatic efficacy in some cases, virtually all the drugs used to treat disorders of mood are potentially lethal when acute over dosage occurs and can cause appreciable morbidity even with careful clinical use.

SUMMARY OF THE INVENTION

The present invention is based on the discovery that leptin levels affect psychological variables, such as carbohydrate craving, sadness and social withdrawals, and mood disorders. As described herein, leptin can directly, or indirectly modulate human emotions. Thus, by increasing or decreasing the levels of leptin (e.g., in the blood or cerebrospinal fluid) mood disorders or psychological parameters such as sadness, carbohydrate craving or social withdrawal (e.g. the need to be left alone in contrast to the need to be with others) can be modulated. As used herein, the term "affective disorder" will include mood disorders such as depression, as well as an affective disorder characterized by alternatives of one or more of the following: psychological variables of sadness, carbohydrate craving or social withdrawal. Other psychological variables, well-known to those of skill in the art, are also intended to be encompassed by this term.

In particular, the present invention relates to the discovery that the symptoms of an affective or mood disorder can be alleviated by altering or modifying leptin levels in the cerebrospinal fluid (CSF) of an individual. In a particular embodiment, CSF leptin levels in an individual with melancholic depression can be increased from the endogenous CSF leptin levels that are present in the individual to decrease or alleviate symptoms of melancholic depression.

In another embodiment, CSF or plasma leptin levels in an individual with atypical depression can be lowered, or decreased, from the endogenous CSF or plasma leptin levels in the individual to decrease or alleviate symptoms of atypical depression. Also encompassed by the present invention are methods of treating atypical depression associated with Cushing's Disease and Chronic Fatigue Syndrome.

In yet another embodiment, CSF or plasma leptin levels in an individual with dysthymia can be lowered, or decreased, from endogenous CSF or plasma leptin levels present in the individual to decrease or alleviate symptoms of dysthymia.

CSF leptin levels in an individual can be altered or modified by altering or modifying endogenous plasma leptin levels and/or endogenous CSF leptin levels in the individual. Increased leptin levels can be achieved by administering to an individual a leptin compound such as exogenous leptin, a leptin analog, biologically active leptin fragment or leptin fusion protein, in an amount sufficient to increase CSF leptin concentration, resulting in a decrease or alleviation of symptoms of depression, e.g., melancholic depression. Decreased leptin levels can be achieved by administering to an individual a leptin antagonist, in an amount sufficient to decrease, or lower, blood or CSF leptin levels, thereby resulting in a decrease or alleviation of symptoms of depression, e.g., atypical depression.

In one embodiment, the invention relates to the use of leptin to treat individuals with forms of affective disorders characterized by higher than normal levels of hypothalamic-pituitary-adrenal (HPA) axis activity. An affective disorder characterized by higher than normal levels of HPA axis activity in accordance with the present invention is treated by administering to an individual in need thereof an effective amount of exogenous leptin, biologically active leptin fragment, or leptin analog or leptin fusion protein. Administration of an effective amount of exogenous leptin, leptin analog, biologically active leptin fragment or leptin fusion protein increases cerebrospinal fluid (brain) leptin levels in the individual. As a result, HPA activity is suppressed in the individual, alleviating symptoms of the disorder.

In still another embodiment, methods for treating dysthymia are provided. In accordance with the invention, dysthymia is treated by administering to an individual in need thereof an effective amount of leptin antagonist. Administering leptin antagonists to the individual increases HPA activity and reduces or alleviates the symptoms of dysthymia.

The invention also relates to methods of treating an affective disorder in an individual in need thereof comprising determining the level of HPA axis activity in the individual and comparing that level with a control level. In accordance with the invention, if the level of HPA axis activity determined in the individual is higher than the control level, an effective amount of exogenous leptin, leptin analog, biologically active leptin fragment or leptin fusion protein is administered to the individual. If the level of HPA axis activity determined in the individual is lower than the control level, an effective amount of leptin antagonist is administered to the individual.

The invention further relates to methods of treating an affective disorder in an individual in need thereof comprising determining the level of corticotrophic-releasing hormone (CRH) production in the individual and comparing that level with a control level. In accordance with the invention, if the level of CRH production determined in the individual is higher than the control level, an effective amount of exogenous leptin, leptin analog, biologically active leptin fragment or leptin fusion protein is administered to the individual. If the level of CRH production determined in the individual is lower than the control level, an effective amount of leptin antagonist is administered to the individual.

The present invention also relates to the discovery that fluctuations in psychometric variables such as mood, stress related behaviors and appetite (e.g., sadness, social withdrawal and carbohydrate craving) can be alleviated by altering or modifying plasma leptin levels of an individual. In a particular embodiment, leptin levels in an individual experiencing sadness or carbohydrate cravings can be increased from the endogenous plasma leptin levels that are present in the individual to decrease or alleviate the psychometric alterations of sadness or carbohydrate craving.

In another embodiment, plasma leptin levels in an individual experiencing social withdrawal can be lowered, or decreased, from the endogenous plasma leptin levels in the individual to decrease or alleviate psychometric symptoms of social withdrawal.

BRIEF DESCRIPTION OF THE DRAWINGS

FIG. 2 is a graphic representation showing 24-hour plasma leptin levels in female patients with either atypical depression or non-atypical depression.

DETAILED DESCRIPTION OF THE INVENTION

Figure 1A:
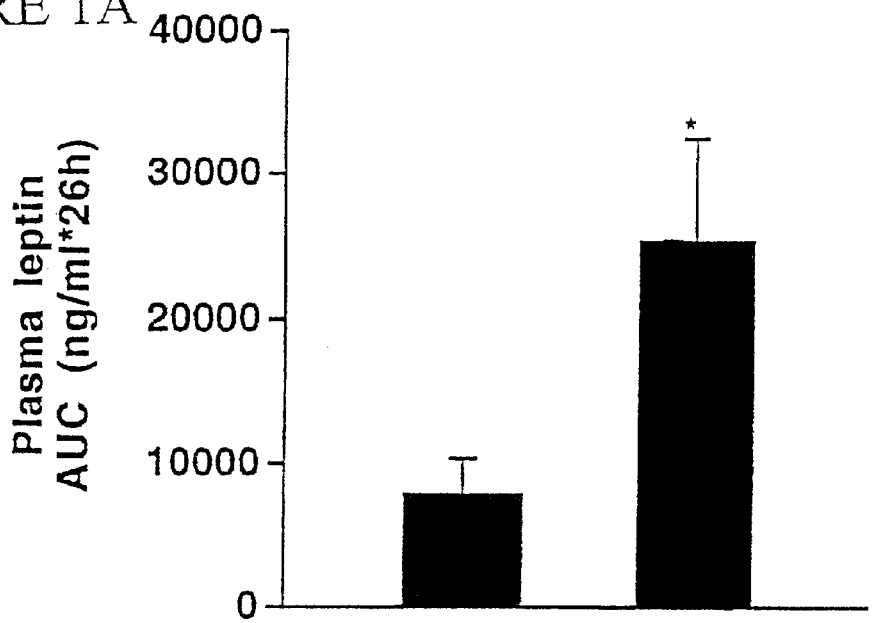
FIGS. 1A–1D are graphic representations showing simultaneous 30-hour plasma (FIGS. 1A and 1C) and cerebrospinal fluid (CSF) (FIGS. 1B–1D) leptin levels in female patients with depression.

The present invention relates to the discovery that leptin levels are increased from normal levels in the blood of patients with an affective disorder characterized by higher than normal levels of HPA axis activity, but are not increased from normal levels in their cerebrospinal fluid. Therefore, even though leptin levels are higher than normal levels in the plasma of these patients, these levels are not high enough to result in increased cerebrospinal fluid leptin levels, which reflect leptin levels in the brain. High cerebrospinal fluid (brain) leptin levels are needed to suppress the increased activity of the HPA axis in these patients.

As defined herein, "normal" levels of leptin means levels of leptin in blood or CSF obtained from individuals not affected by a mood disorder. Typically levels of blood and CSF leptin are determined by assay as described herein. "Normal" levels of HPA axis activity is defined herein as to mean levels of HPA axis activity in individuals not affected by a mood disorder. Typically physiological parameters of HPA axis activity include measurements of corticotrophin-releasing hormone (CRH) and ACTH, and may also include measurement of other hormones, e.g., corticosteroids. Assays for measuring these hormones are well known to those of skill in the art. HPA axis activity can also be evaluated by behavioral parameters such as sleep disturbances, appetite, libido and psychometric alterations.

Additionally, as described herein, fluctuations in plasma leptin levels are associated with simultaneous fluctuating (e.g., alterations) psychometric variables. Alterations in psychometric variables (also referred to herein as parameters) can include, for example, alterations in carbohydrate craving, sadness and social withdrawal (e.g., the need to be left alone, in contrast to the need to be with others). Psychometric alterations can be evaluated using established techniques. For example, symptom ratings can be assessed by the patient using a visual-analog self-rating score system (Folstein, M. F. et al., *Psychol. Med.* 3:479–476 (19973)). The effects of plasma and CSF leptin levels on behavioral parameters, psychometric alterations or both can also include effects not mediated by the HPA axis. Thus, leptin can be used to treat patients with or without affective disorders who experience variations in psychometric parameters.

The present invention further relates to the discovery that serum leptin levels in healthy patients are related to psychometric disorders. For example, feelings of sadness and carbohydrate cravings are inversely related to serum leptin levels and social withdrawal is directly related to serum leptin levels. In one embodiment, an individual experiencing sadness or elevated carbohydrate cravings can be treated with leptin, leptin, analog, biologically active leptin fragment or a leptin fusion protein to decrease or alleviate the symptoms of sadness or carbohydrate craving. In another embodiment an individual experiencing social withdrawal can be treated with a leptin antagonist to decrease leptin levels and decrease or alleviate the symptoms of social withdrawal.

The present invention also relates to the discovery that plasma leptin levels are higher than normal in patients with an affective disorder characterized by lower than normal levels of HPA axis activity. It is reasonable to believe that high levels of leptin excessively suppress HPA activity in these patients and contribute to the symptoms of the disorder.

Leptin is inversely related to pituitary-adrenial function, and that in humans, high leptin levels decrease activity of the hypothalamic-pituitary-adrenal (HPA) axis, while low leptin levels increase activity of the HPA axis. Human leptin levels are pulsitile and inversely related to pituitary-adrenal functions (U.S. Ser. No. 08/749,534, the teachings of which are herein incorporated by reference).

Thus, the present invention encompasses methods of treating an affective disorder in an individual comprising administering an effective amount of exogenous leptin, leptin analog, biologically active leptin fragment, leptin fusion protein, or leptin antagonist to the individual. The exogenous leptin, leptin analog, biologically active leptin fragment, leptin fusion protein or leptin antagonist can be administered in single or multiple doses.

As used herein, the term "affective disorder" refers to a mental disorder characterized by neuroendocrine dysregulation and by a disturbance in the regulation of mood, behavior, emotions such as sadness, social withdrawal and carbohydrate cravings, and affect. Affective disorders are also referred to herein as mood disorders and include, for example, major depressive disorders, such as melancholic depression, atypical depression as well as chronic mood disorder such as dysthymia and anxiety disorders.

The present invention relates to the use of leptin, leptin analogs, biologically active leptin fragments and leptin fusion proteins in the treatment of affective disorders characterized by higher than normal levels of HPA axis activity. An affective disorder characterized by higher than normal levels of HPA axis activity includes forms of depression characterized by higher than normal levels of HPA axis activity, such as melancholic depression.

The present invention also relates to the use of leptin antagonists in the treatment of affective disorders characterized by lower than normal levels of HPA axis activity. An affective disorder characterized by lower than normal levels of HPA axis activity includes forms of depression characterized by lower than normal levels of HPA axis activity, such as atypical depression.

In a particular embodiment, methods of treating an affective disorder in an individual comprise determining the level of HPA axis activity in the individual and comparing that level with a control level. In accordance with the invention, if the level of HPA axis activity determined in the individual is higher than the control level, an effective amount of exogenous leptin, leptin analog, biologically active leptin fragment or leptin fusion protein is administered to the individual. If the level of HPA axis activity determined in the individual is lower than the control level, an effective amount of leptin antagonist is administered to the individual. As used herein, the control level of HPA axis activity refers to the level of HPA axis activity in a healthy individual not suffering from an affective disorder or experiencing neuroendocrine dysfunction, matched for age, sex and BMI with the individual to be treated.

In another embodiment, methods of treating affective disorders in an individual comprise determining the level of CRH production in the individual and comparing that level with a control level. In accordance with the invention, if the level of CRH production determined in the individual is higher than the control level, an effective amount of exogenous leptin, leptin analog, biologically active leptin fragment or leptin fusion protein is administered to the individual. If the level of CRH production determined in the individual is lower than the control level, an effective amount of leptin antagonist is administered to the individual. As used herein, the control level of CRH refers to the level of CRH in a healthy individual not suffering, from an affective disorder or experiencing neuroendocrine dysfunction, matched for age, sex and BMI with the individual to be treated.

CRH can be evaluated in an individual at one or more time points using suitable techniques. CRH levels can be measured in blood (e.g., plasma) or CSF. For example, level of CRH production can be determined by immunoassay. A variety of suitable immunoassays are known to those of skill in the art. For example, the level of CRH production in an individual can be determined by radioimmunoassay (RIA) or enzyme-linked immiunosorbent assay (ELISA).

Leptin is the product of the obese (ob) gene and is secreted by adipose cells (Zhang, et al., *Nature*, 372:425–432 (1994)). Leptin receptors are found in the choroid plexus and the hypothalamus. (Tartaglia, L. A., *Cell*, 83:1263–1271 (1995)). The action of leptin to regulate energy balance appears to be primarily through effects in the brain, in particular the hypothalamus. A rising, level of leptin, as triglyceride stores increase, is proposed to serve as a negative feedback signal to the brain, resulting in decreased food intake, increased energy expenditure and resistance to obesity. In addition, circulating leptin appears to play an important role in the neuroendocrine axis (Ahima, R.S. et al., *Nature*, 382:250–252 (1996)).

It has recently been shown that leptin levels are inversely related to pituitary-adrenal function and that in humans, high leptin levels seem to decrease HPA axis activity, while low leptin levels seem to increase HPA axis activity (Licinio et al., *Nature Med.*, 3:575–579 (1997)). It has also been shown that in humans, serum leptin concentrations vary with the percentage of body fat, and that during weight loss, serum leptin concentrations initially decline, but increase again during maintenance of the lower weight (Considine et al., *N. Eng. J. Med.*, 334:292–295 (1996)).

Leptin can be recombinantly produced as described in e.g., WO 96/05309; U.S. Pat. No. 5,552,522; U.S. Pat. No. 5,552,523; and U.S. Pat. No. 5,552,524, the teachings of which are incorporated by reference. Leptin can also be produced by chemical synthesis, or isolated from mammalian plasma using methods well-known to those of skill in the art. The exogenous leptin administered in the present methods can be intact protein, e.g., the full-length 167 amino acid polypeptide as described in Zhang. Y. et al., *Nature*, 372:425–432 (1994).

Leptin used in the present methods can also be a functional or biologically active equivalent of the leptin protein described above. A "functional or biologically active" equivalent is defined herein as a protein which shares significant amino acid sequence identity with the corresponding sequence of the endogenous, or naturally-occurring protein (e.g., typically about 80% sequence identity, more typically about 90% sequence identity and most typically about 95% sequence identity) and possesses at least one, or more, of the biological functions thereof. Biological functions include antigenic, immunogenic, and structural properties, anti-obesity activity, such as activity to reduce weight, appetite and mobilize fat, and hypothalamic-regulating activity. Antigenicity is defined herein as the ability of the protein or analog to bind to anti-leptin antibodies. Immunogenicity is defined herein as the ability of the protein or analog to induce the production of antibodies that specifically react with endogenous leptin. These properties and activities can be a measure of biological function.

Specifically included in the present invention are leptin analogs, or derivatives, defined herein as proteins having amino acid sequences analogous to endogenous leptin. Analogous amino acid sequences are defined herein to mean amino acid sequences with sufficient identity of amino acid sequence of endogenous leptin to possess the biological activity of endogenous leptin, but with one or more "silent changes" in the amino acid sequence. A "silent" amino acid change means that one, or more residues differ from the endogenous amino acid sequence. Examples of such differences include additions, deletions, or substitutions of residues, as well as analogous proteins that exhibit greater, or lesser activity than edogenous leptin.

Also encompassed by the present invention is the administration of biologically active polypeptide fragments of leptin. Such fragments can include only a part of the full-length amino acid sequence of leptin, yet possess biological activity. Such fragments can be produced by carboxyl or amino terminal deletions, as well as internal deletions. Such polypeptides can be tested for biological activity as described herein. Biologically active analogs and fragments of leptin useful in the present invention are described, e.g., in WO 96/05309; U.S. Pat. No. 5,552,522; U.S. Pat. No. 5,552,523; and U.S. Pat. No. 5,552,524, the teachings of which are incorporated by reference.

The present invention also encompasses the administration of fusion proteins comprising leptin proteins as described herein, referred to as a first moiety, linked to a second moiety not occurring in the leptin protein. The second moiety can be a single amino acid, peptide or polypeptide or other organic moiety, such as a carbohydrateor, a lipid, or an inorganic molecule. Examples of a second moiety include maltose or glutathione-S-transferase.

Also encompassed by the present invention are biologically active derivatives or analogs of leptin referred to herein as leptin peptide mimetics. These mimetics can be designed and produced by techniques known to those of skill in the art. (See e.g., U.S. Pat. Nos. 4,612,132; 5,643,873 and 5,654,276, the teachings of which are herein incorporated by reference). These mimetics are based on the leptin sequence, and peptide mimetics possess biologically activity (i.e., leptin activity) similar to the biological activity of the corresponding peptide compound, but possess a "biological advantage" over the corresponding peptide inhibitor with respect to one, or more, of the following properties: solubility, stability, and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic inhibitor. The following are examples of modifications of peptides to produce peptide mimetics as described in U.S Pat. Nos: 5,643,873 and 5,654,276, the teachings of which are incorporated herein by reference.

Increased leptin levels can be achieved by the administration of exogenous leptin or, alternatively, by increasing endogenous leptin production, for example by stimulating the endogenous gene to produce increased amount of leptin. In some individuals the amount of leptin being produced can be of sufficient quantity, but the leptin is abnormal in some way and, thus, cannot exert its biological effect. In this instance, providing copies of normal leptin genes to adipocytes, using techniques of gene transfer well-known to those of skill in the art, can increase leptin levels.

The present invention further encompasses the administration of leptin antagonists. As used herein, a leptin antagonist decreases, blocks, inhibits, abrogates or interferes with leptin biological function or activity or receptor signaling in vivo. Leptin antagonists include anti-leptin antibodies, receptor molecules and derivatives which bind specifically to leptin and prevent leptin from binding to its cognate receptor.

Leptin antagonists also include agents, or drugs, which decrease, inhibit, block, abrogate or interfere with binding of leptin to its receptors or extracellular domains thereof; agents which decrease, inhibit, block, abrogate or interfere with leptin production or activation; and agents which are antagonists of signals that drive leptin production or synthesis. Such an agent can be any organic molecule that inhibits or presents the interaction of leptin with its receptor, or leptin production.

Candidate receptor antagonists can be identified by evaluating the binding of leptin to its receptor in the presence of, and absence of, the candidate antagonist. Such techniques are well-known to those of skill in the art. Leptin antagonists so identified can be further tested in-vivo for leptin antagonist activity.

The methods of the present invention can be accomplished by the administration of leptin, leptin analogs, biologically active leptin fragments, leptin fusion proteins or leptin antagonists by parenteral or enteral means. Routes of administration encompassed by the present invention include intravenous, intraarterial, intraperitoneal, intramuscular or subcutaneous routes, as well as oral and nasal administration. Suppositories or transdennal patches can also be used.

Leptin, leptin analogs, biologically active fragments, fusion proteins and leptin antagonists can be administered as leptin compositions in admixture with conventional excipients, i.e., pharmaceutically, or physiologically, acceptable organic, or inorganic carrier substances suitable for parenteral or enteral application which do not deleteriously react with the active leptin. Suitable pharmaceutically acceptable carriers include, e.g., water, salt solutions, alcohols, oils, gelatins and carbohydrates. Leptin, leptin analogs, biologically active fragments, fusion proteins and leptin antagonists can also be incorporated into liposomes or administered via transdermal patches. Pharmaceutical compositions suitable for use in the present invention are well-known to those of skill in the art and are described e.g., in WO 96/05309, the teachings of which are hereby incorporated by reference.

An "effective amount" of leptin, leptin analog, biologically active fragment, leptin fusion protein or leptin antagonist is defined herein as that amount, or dose, of leptin, leptin analog, biologically active fragment, leptin fusion protein or leptin antagonist that, when administered to a mammal, is sufficient for therapeutic efficacy (e.g., an amount sufficient for significantly reducing or eliminating signs or symptoms associated with a particular affective disorder).

Plasma and CSF leptin levels are strongly correlated in a non-linear manner, and CSF leptin levels can be modified by peripheral administration of exogneous leptin. For example, Schwartz, M. W., et al., (Nature Medicine 2:589 (1996)) describes the relationship between plasma and CSF leptin as the following: $y=0.0047x+0.0404 \text{ Log}_e x+0.0486$, where y=CSF leptin, and x=plasma leptin.

The dosage administered to an individual will vary depending upon a variety of factors, including the phaiiacodynamic characteristics of the particular leptin analog, biologically active fragment, leptin fusion protein or leptin antagonist, and its mode and route of administration; size, age, sex, health, body weight, body mass index (BMI), and diet of the recipient; nature and extent of symptoms of the disorder being treated, kind of concurrent treatment, frequency of treatment, and the effect desired.

Leptin, leptin analogs, biologically active fragments, leptin fusion proteins or leptin antagonists can be administered in single or multiple doses depending upon factors such as nature and extent of symptoms, kind of concurrent treatment and the effect desired. Other therapeutic regimens or agents can be used in conjunction with the methods and leptin, leptin analogs, biologically active fragments, leptin fusion proteins and leptin antagonists of the present invention. Adjustment and manipulation of established dosage ranges are well within the ability of those skilled in the art.

The present invention is further illustrated by the following examples, which are not intended to be limiting in any way.

EXAMPLE 1: PLASMA AND CEREBROSPINAL FLUID LEPTIN LEVELS IN PATIENTS WITH DEPRESSION

Four depressed female patients, with an average age of 30 years were enrolled in this study. A control group of three healthy female adults, matched for age and BMI, were also enrolled in the study. None of the subjects were morbidly obese.

All subjects underwent a 30 hour blood and spinal fluid sampling period starting at 10:00 am. Blood and spinal fluid were simultaneously drawn through an indwelling catheter at one hour intervals.

Leptin was measured by radioimmunoassay (RIA). Aliquots(50 µl) of test plasma or 50 µl of test cerebrospinal fluid (concentrated 5×) was incubated for 24 hour at 4° C. with phosphate-buffered saline (PBS) containing 0.1% Triton X-100 and a 1:2000 dilution of anti-leptin antiserum. Twenty-four (24) hours later $^{125}$I-labeled leptin (approximately 15,000 cpm) was added to the tube and the reagents were incubated for an additional 24 hours. Antibody-bound leptin was precipitated by addition of 500 µl of precipitating reagent. Tubes were centrifuged for 45 minutes at 2,500 rpm, after which supernatants were decanted and pellets counted in a gamma counter. For this leptin assay, the limit of detection is 0.2 ng/ml; within-assay coefficient of variation (CV) was 4.4% for low levels (2.9 ng/ml) and 5.7% for high levels (14.1 ng/ml). Interassay CV was 6.9% and 9% for low and high levels, respectively. Values were analyzed by ANOVA.

Results

Figure 1B:
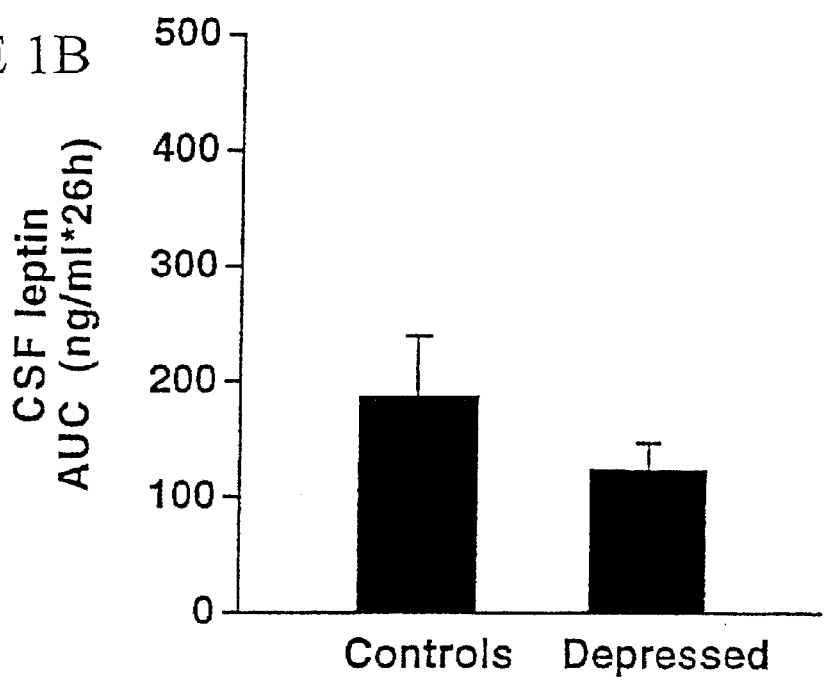
Figure 1C:
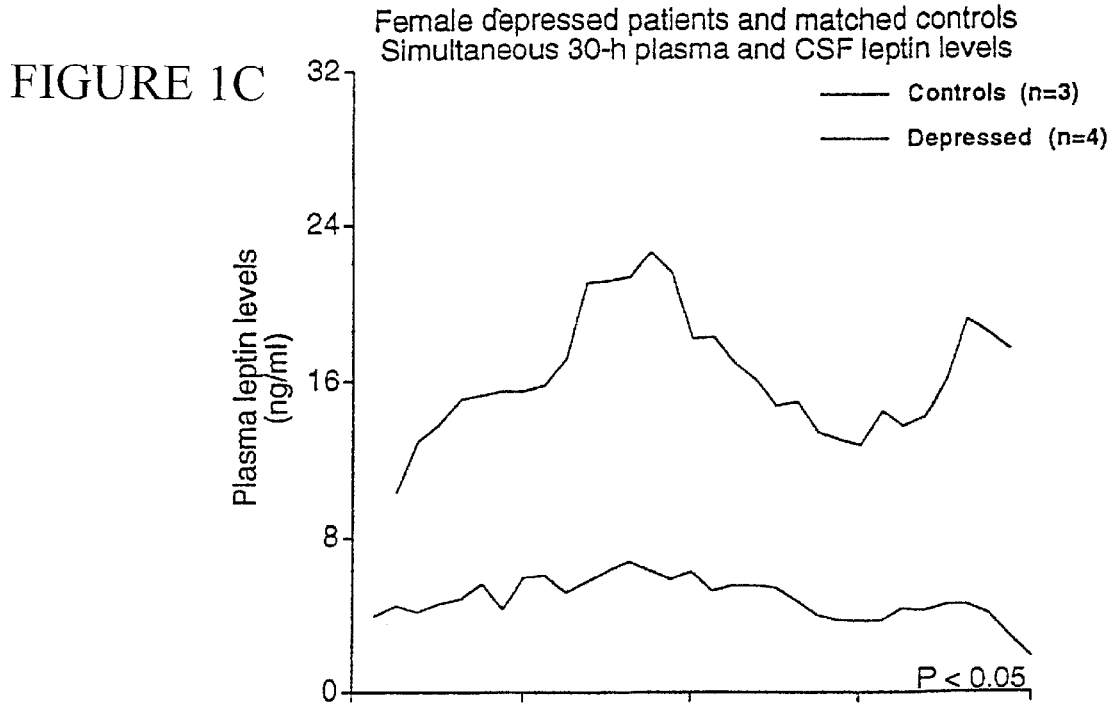
Figure 1D:
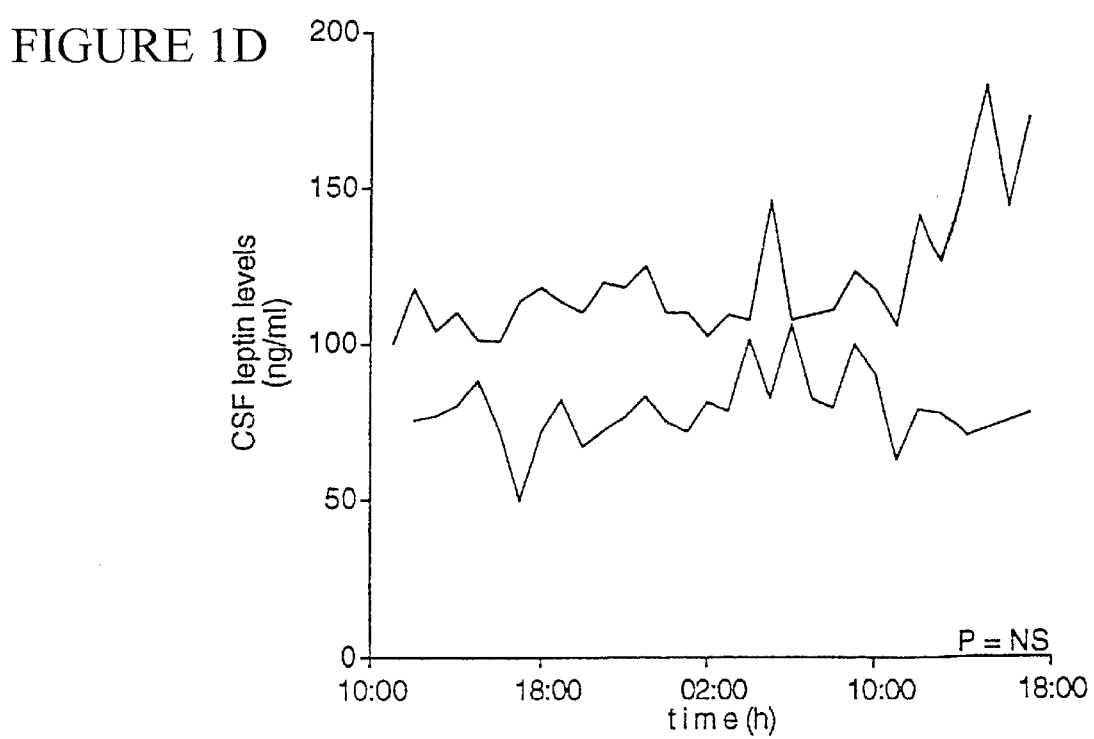

As a group, the patients with depression had significantly increased plasma leptin levels as compared to the healthy controls (FIGS. 1A and 1C). Cerebrospinal fluid leptin levels, which reflect leptin levels in the brain, did not differ significantly between the depressed patients and healthy controls (FIGS. 1B and 1D). Thus, although plasma leptin levels were higher in the depressed patients than in the healthy controls, these levels were not high enough to result in increased cerebrospinal fluid (brain) leptin levels.

EXAMPLE 2: PLASMA LEPTIN LEVELS IN PATIENTS WITH ATYPICAL DEPRESSION

One female patient diagnosed with atypical depression and three female patients diagnosed with depression (non-atypical) (average age of 30 years), were enrolled in this study. One healthy female adult was also enrolled as a control subject. None of the subjects were morbidly obese. Diagnosis of depression (atypical and non-atypical) was made using the DSM-IV. The patient with atypical depression suffered from hypersomnia, increased food intake, weight gain and fatigue.

All subjects underwent a 24 hour blood sampling period starting at 08:00 am. Blood was drawn through an indwelling forearm catheter. In the patient with atypical depression, blood was drawn at 7 minute intervals. For all other subjects, blood was drawn at one hour intervals.

Leptin was measured by RIA. 50 µl of test plasma was incubated for 24 hour at 4° C. with PBS containing 0.1% Triton X-100 and a 1:2000 dilution of anti-leptin antiseuim. Twenty-four (24) hours later $^{125}$I-labeled leptin (approximately 15,000 cpm) was added to the tube and the reagents were incubated for an additional 24 hours. Antibody-bound leptin was precipitated by addition of 500 µl of precipitating reagent. Tubes were centrifuged for 45 minutes at 2,500 rpm, after which supernatants were decanted and pellets counted in a gamma counter. For this leptin assay, the limit of detection is 0.2 ng/ml; within-assay coefficient of variation (CV) was 4.4% for low levels (2.9 ng/ml) and 5.7% for high levels (14.1 ng/ml). Interassay CV was 6.9% and 9% for low and high levels, respectively. Values were analyzed by ANOVA.

Results

The patient with atypical depression had significantly higher plasma leptin levels as compared to the healthy control and the patients with non-atypical depression (FIG. 2). This suggests that high leptin levels in patients with atypical depression contribute to their symptoms of hypersomnia, increased food intake, weight gain and fatigue.

EXAMPLE 3: PLASMA LEPTIN LEVELS AND PSYCHOMETRIC VARIABLES IN HEALTHY PATIENTS

Fluctuations in plasma leptin concentrations throughout the day are correlated with simultaneous fluctuations in psychometric variables such as mood, stress related behaviors, and appetite. Ten healthy normal-weight subjects (5 males, 5 females), [body mass index (BMI)=23.4±0.9 kg/m$^2$, age=29.5±2.2 years] were admitted to a clinical research unit at the Clinical Center at NIH. Informed consent was obtained prior to all procedures. Blood samples for the determination of leptin were drawn via a venous catheter from each subject at 7 minute intervals for 24 hours starting at 8:00 a.m., as previously described (Licino, J., et al., *Proc. Natl. Acad. Sci* 95:2541–2546 (1998)). Plasma leptin concentrations were determined by radioimmunoassay (Lucinio, J., et al., *Nat. Med.* 3:575–579 (1997)) and values were averaged at 1 hour intervals. Symptom ratings were obtained from a 100-mm visual-analog self-rating scores for eight emotional states: sadness, social withdrawal, appetite, carbohydrate craving, concentration, tiredness, self-esteem and physical discomfort (Folstein, M. F., et al., *Psychol. Med.* 3:479–486 (1973)). Each subject completed the self-ratings hourly from 09:00 until 23:00 h, simultaneously with the blood collection. Meals were served at 8:30 AM (breakfast), 12:30 PM (lunch), 17:30 PM (dinner) and 21:00 PM (evening snack).

Figure 3:
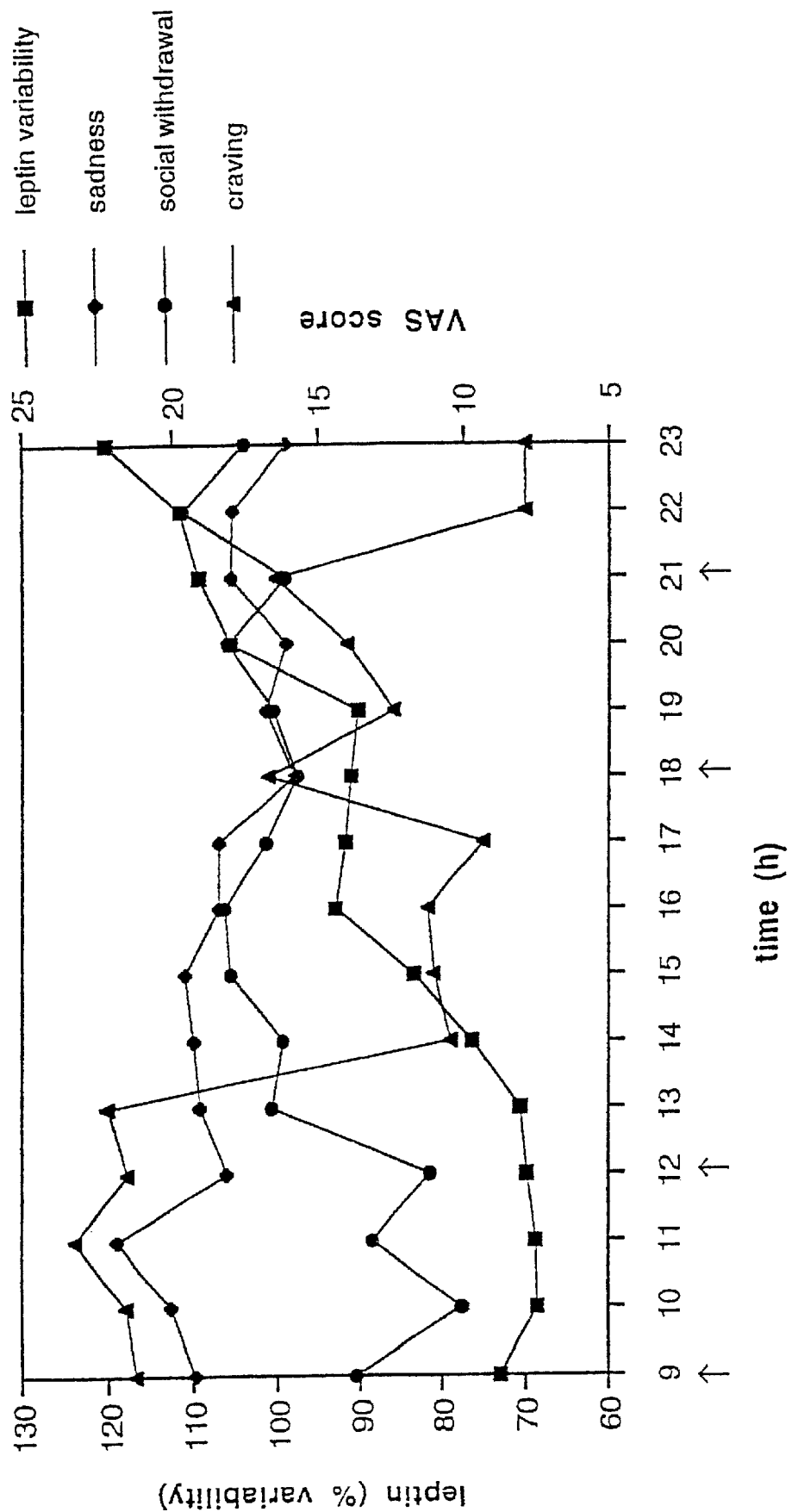
FIG. 3 is a temporal display of psychological states (sadness, social withdrawal, carbohydrate craving) and leptin variability during a 24 hour period. Visual analog scores (VAS) are averaged from patients. Meals were served as timepoints indicated by the arrows.
Figure 4A:
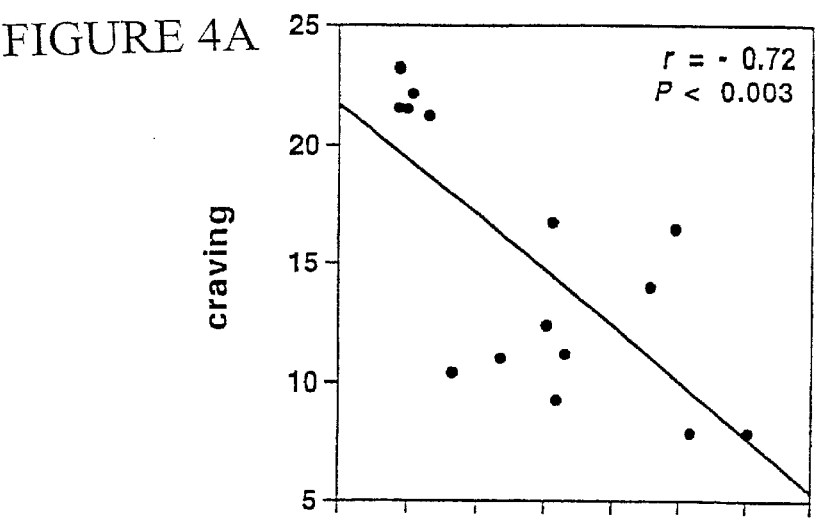
FIGS. 4A–4C are graphic representations showing plasma leptin levels inversely correlated with carbohydrate cravings (FIG. 4A); inversely correlated with sadness (FIG. 4B); and positively correlated with social withdrawal (FIG. 4C).
Figure 4B:
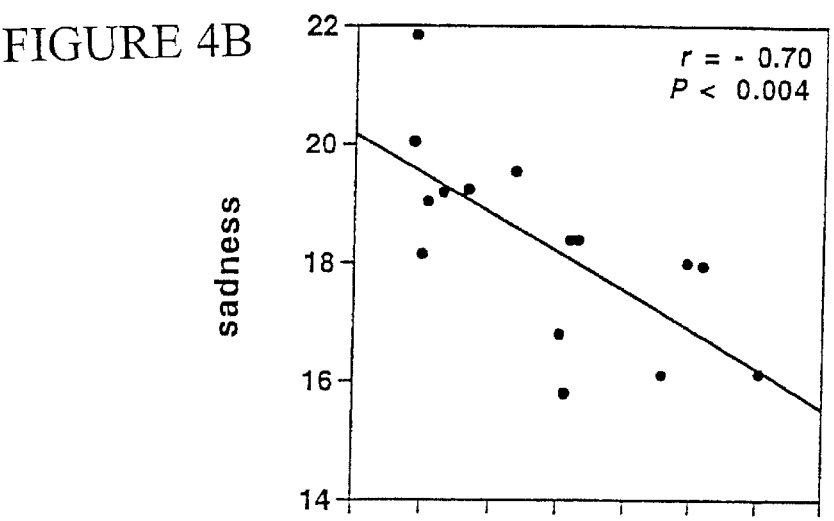
Figure 4C:
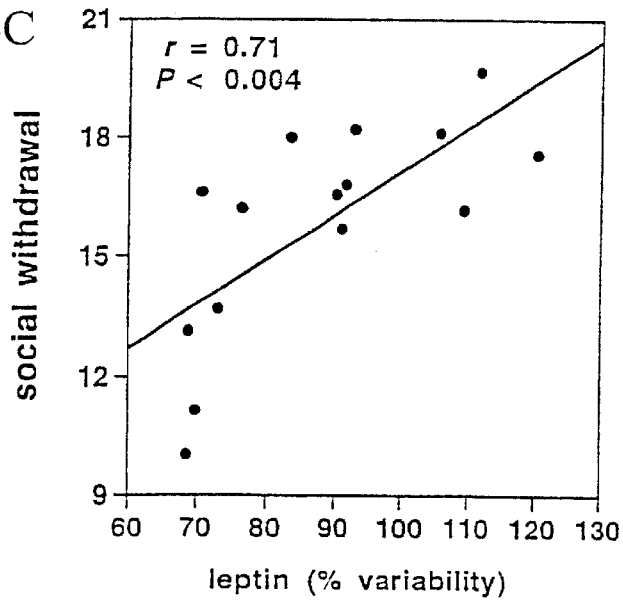

FIG. 3 shows the time course of leptin variability and psychometric variables from 08:00 until 23:00 h, during which psychometric variables were assessed. Leptin variability is defined as a percentage of individual 24-hour average, using the formula: variability at time t=(hormone level at time t/24-h individual average level)×100. A higher score in the visual analog scale measurement indicates more pronounced symptoms. Social withdrawal, concentration, self-esteem and physical discomfort were considered as measures analogous to behaviors observed in animal models of stress (Chrousos, G. P., et al., *JAMA* 257:1244–1252 (1992)). Using linear regression (Pearson's correlation), the craving for carbohydrates (r=0.72; P<0.003), social withdrawal (r=0.71; P<0.003) and sadness (r=0.70; P<0.004) were highly and significantly correlated with leptin variability. The other subjective psychological states did not show significant correlation with leptin levels. Significancy was calculated taking into consideration multiple comparisons (Bonferroni's correction). A highly significant negative correlation between leptin variability and craving indicating that an increase in leptin levels was accompanied by similar decrease in the subjective feeling of carbohydrate craving (FIG. 4A). A highly negative correlation was also found when sadness and leptin variability were compared (FIG. 4B). Social withdrawal had a highly positive correlation with leptin levels (FIG. 4C). The temporal correlation among the emotional states and leptin during 16 hours can be seen in FIG. 3. There is a clear increase in leptin values throughout the day which is followed by a similar pattern in the social withdrawal scores. Craving for sugar and sadness have a tendency to diminish towards the end of the day, indicating an hourly negative correlation between leptin and both scores.

The present invention shows that fluctuations in longitudinally-sampled leptin concentrations are temporally correlated with psychometric variables. The effects of leptin on food intake can explain the negative correlation observed with craving. No correlation between appetite and leptin was observed, which further supports the concept that leptin is not a short term satiety factor. During the course of the day increases in leptin level are associated with decreased search for starchy foods, decreased feelings of sadness and increased social withdrawal (FIGS. 3 and 4A, 4B, 4C). Sadness and social withdrawal are key symptoms of major depression, a disorder which has been postulated to involve abnormal CRH activity (Gold, P. W., et al., *N.Engl. J. Med.* 319:348–353 (1998)).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of treating an affective disorder in an individual, wherein the affective disorder is characterized by alterations in one, or more of the following psychometric variables: sadness, carbohydrate craving, or social withdrawal, comprising administering to the individual an effective amount of leptin, leptin analog, biologically active leptin fragment, leptin fusion protein or leptin antagonist.

2. A method of treating dysthymia in an individual in need thereof comprising administering to the individual an effective amount of a leptin antagonist, wherein the leptin antagonist is administered in a single dose.

3. A method of treating an affective disorder characterized by a psychometric variable in an individual comprising administering to the individual an effective amount of leptin, leptin analog, biologically active leptin fragment, leptin fusion protein or leptin antagonist.

4. The method of claim 3 wherein the psychometric variable is selected from the group consisting of: sadness, social withdrawal and carbohydrate craving.

5. The method of claim 3 wherein the leptin, leptin analog, leptin fragment, leptin fusion protein or leptin antagonist is administered in a single dose.

6. The method of claim 3 wherein the leptin, leptin analog, leptin fragment, leptin fusion protein or leptin antagonist is administered in multiple doses.

* * * * *